United States Patent [19]

Snyder

[11] 3,954,411
[45] May 4, 1976

[54] PREPARATION OF REAGENTS ON-LINE IN AUTOMATED SAMPLE ANALYSIS

[75] Inventor: Lloyd R. Snyder, Yorktown Heights, N.Y.

[73] Assignee: Technicon Instruments Corporation, Tarrytown, N.Y.

[22] Filed: Feb. 11, 1974

[21] Appl. No.: 441,540

[52] U.S. Cl. .............................. 23/230 R; 23/230 B; 23/230.3; 23/230.6; 23/253 R; 195/101
[51] Int. Cl.² ................ G01N 31/04; G01N 33/00; G01N 33/16
[58] Field of Search .......... 23/230 R, 230 B, 253 R; 195/101, 103.5 R, 127

[56] References Cited
UNITED STATES PATENTS

| | | | |
|---|---|---|---|
| 2,797,149 | 6/1957 | Skeggs | 23/230 R |
| 3,114,609 | 12/1963 | Jones | 23/230 R |
| 3,376,114 | 4/1968 | Eberle | 23/230 B |
| 3,600,135 | 8/1971 | Davis | 23/253 R |
| 3,615,234 | 10/1971 | Ludvigsen | 23/253 R |
| 3,699,004 | 10/1972 | Skeggs | 23/253 R X |
| 3,785,771 | 1/1974 | Luchsinger et al. | 23/230 R |
| 3,788,812 | 1/1974 | Dupre | 23/230 R |
| 3,796,543 | 3/1974 | Kamphake | 23/230 R |

*Primary Examiner*—Joseph Scovronek
*Attorney, Agent, or Firm*—S. P. Tedesco; Stephen E. Rockwell

[57] ABSTRACT

Method and apparatus in an automated sample analysis system for on-line preparation from plural constituents of a reagent for combination with a sample, which includes purification of the reagent prior to exposure of the reagent in a flowing stream to a flowing stream of such sample. For such reagent preparation, the fluid constituents are caused to flow in respective streams which combine in the required volumes in a predetermined sequence to form a resultant stream in which the constituents intermingle and interact. This stream passes through a purifier as it flows toward a confluence with the sample stream, to free the reagent from one or more elements which would interfere with sample analysis.

7 Claims, 2 Drawing Figures

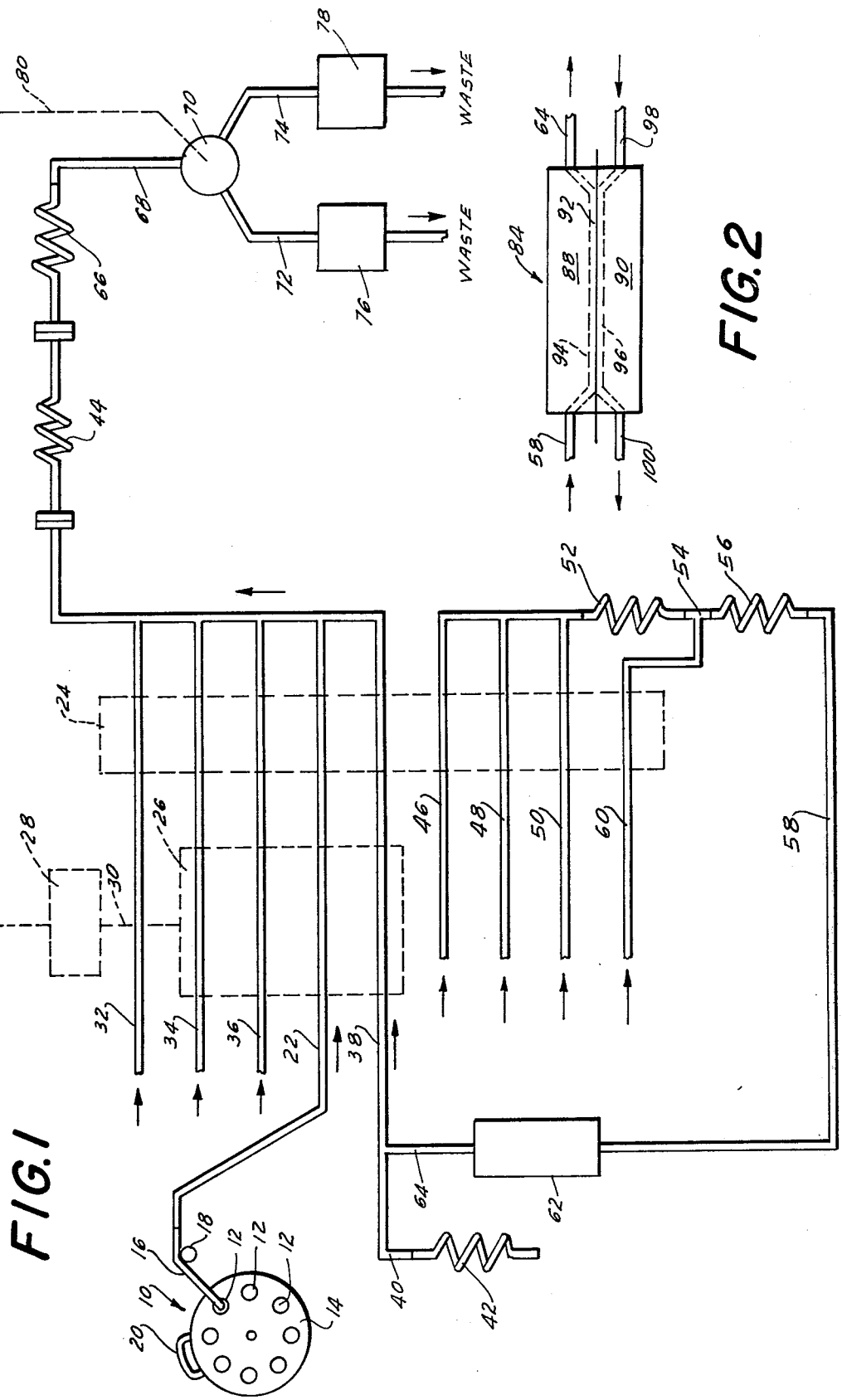

PREPARATION OF REAGENTS ON-LINE IN AUTOMATED SAMPLE ANALYSIS

BACKGROUND OF THE INVENTION

1. Field of the Invention

The invention relates to the preparation on-line in an automated sample analysis system of a reagent for exposure in such system to sample.

2. Prior Art

Previously manufactured and bottled reagents have been utilized frequently to supply the liquid substances necessary for a particular reaction with a sample liquid in automated quantitative analysis of such sample in apparatus of the general type described in Skeggs U.S. Pat. No. 2,797,149 issued June 25, 1957. Further, unstable reaction products have been produced on-line in other uses of such apparatus where such products subsequently react on-line in the same apparatus with samples in tests requiring use of such unstable products as reagents. Such on-line production of reagents in such analyses often result in the presence in such apparatus of undesirable by-products or other elements which interfere with sample analyses. The present invention contemplates such reagent production with the removal of such by-products or other interfering elements.

SUMMARY OF THE INVENTION

It is an object of the invention to provide an improved system for automated quantitative analysis of liquid samples for a constituent of interest. Another object is to provide such a system for on-line preparation from plural constituents of a reagent for combination with a sample, which includes purification of the reagent prior to exposure of the reagent to a flowing stream of such sample. The invention includes a method and apparatus for such analysis wherein the fluid constituents for such reagent production are caused to flow in respective streams which combine in the required volumes in a predetermined sequence to form a resultant stream in which the constituents mix and react chemically or otherwise with one another. This stream in which some or all of the constituents are reacted is passed through a purifier as it flows toward a confluence with the sample stream, to free the reagent from one or more elements which would interfere with sample analysis.

BRIEF DESCRIPTION OF THE DRAWING

In the drawing:

FIG. 1 is a diagrammatic view of a quantitative sample analysis system embodying the invention; and FIG. 2 is a fragmentary diagrammatic view illustrating a modification of such system.

DETAILED DESCRIPTION OF THE PREFERRED EMBODIMENT

For purposes of example only and not by way of limitation, the form of the invention chosen for illustration involves an immunological test of sample and in this particular example the reagent which is produced on-line is an antigen bearing a label of a radioactive type. Also, for purposes of this description, an antigen as referred to herein includes any chemical species which is capable of undergoing, either directly or as a hapten derivative, an immunochemical reaction with an antibody and includes various peptides and proteins, such as the hormones insulin and HGH, enzymes, transport proteins like albumin and immunoglobulins such as IgG. Such antigens also include the non-peptide hormones such as steroids, vitamins, therapeutic drugs such as digoxin, viral antigens such as Australian antigen for hepatitis for example, and almost all chemical substances involved in living organisms other than the simplest molecules such as glucose and urea for example. In the chosen example, the quantitative sample analysis is for HGH, an antigen, in human blood specimens.

In the form of the invention shown in FIG. 1, a sampler, indicated generally at 10, is provided to supply, for example, a series of human blood plasma or serum samples for analysis. Each of the samples is separately supported in a cup 12 of a series of cups supported on a motor-driven turntable 14 of the sampler. Associated with the sampler is a conventional movable probe 16 provided on support 18 for movement of the probe into the cup indexed at an offtake station for aspiration of the sample and then into circulating liquid within a wash receptacle 20 for rinsing of the probe in the wash liquid before the probe 16 enters the next sample cup after movement of the turntable 14. Between immersions in sample and wash liquid the probe 16 aspirates air. The sampler may be of the general type described in de Jong U.S. Pat. No. 3,134,263 issued May 26, 1964.

The stream flowing from the probe 16 is conveyed through the coupled inlet end of a compressible pump tube 22 under the action of a pump 24 which may be of a conventional peristaltic type such as that described in Bilichniansky U.S. Pat. No. 3,425,357, issued Feb. 4, 1969. Intermediate the last-mentioned end of the tube 22 and the pump 24, the tube extends through a pinch valve assembly 26, which on command from a controller such as a timer 28, pinches the tube 22 to completely block flow therethrough. A lead 30 interconnects an output of the timer 28 to an input of the valve assembly 26.

A compressible pump tube 32, having an inlet end open to the ambient atmosphere to aspirate gas such as air, extends through the pump 24. Compressible pump tubes 34, 36 and 38 extend through the pinch valve assembly 26 and the pump 24. The valve assembly 26 is operative in a first condition to pinch shut the tube 34 to stop flow therethrough while tubes 22, 36 and 38 convey fluids, and in a second condition to simultaneously pinch shut and stop flow in tubes 22, 36 and 38 while allowing flow in pump tube 34, the valve assembly being switched from one condition to the other at intervals controlled by the timer 28. The inlet end of the tube 34 is coupled to a non-illustrated source of rinse solution. The inlet end of the tube 36 is coupled to a non-illustrated source of antibody $Ab_1$ in solution which constitutes a reagent. Antibody $Ab_1$ may be produced in a rabbit and is specific for human HGH, the antigen under assay which antigen Ag is a peptide. The pump tube 38, which aspirates the previously mentioned labeled or radioactive reagent, has an end 40 on the suction side of the pump 24. The tube end 40, which is both an inlet and an outlet as will appear hereinafter, is coupled to one end of a labeled-reagent storage coil 42. The outlet ends of the tubes 22, 32, 34 and 36 are coupled to the tube 38 intermediate the ends of the latter but on the pressure side of the pump 24 and in the relationship to one another indicated in FIG. 1. The outlet end of the tube 38 is coupled to the inlet end of an incubation coil 44.

The timer 28 controls the pinch valve assembly 26 in timed relation to the movements of the probe 16. The mode of operation of the valve assembly 26 is hereinafter described. When the probe 16 is immersed in the wash solution in receptacle 20, pump tube 34, previously pinched shut by the assembly 26 in the first condition thereof, is released by the assembly 26 in the second condition thereof. Rinse solution, aspirated at a rate of 0.6 ml/min. for example, flows through the tube 34 into pump tube 38 where it is segmented by gas from pump tube 32 aspirated at a rate of 0.3 ml/min. for example. Concurrently with such flow in the tube 34, the assembly 26, then in the second condition, stops flow in the pump tubes 22, 36 and 38 so that no wash solution in receptacle 20 is aspirated by the probe and no reagents flow in the pump tubes 36 and 38.

When the probe 16 leaves the wash receptacle in its travel toward the first sample in a cup 12 at the offtake station, the valve assembly 26 is returned to the first condition to stop flow in tube 34 and allow flow in pump tubes 22, 36 and 38, so that air aspirated through the probe 16 flows through tube 22 into tube 38 on the pressure side of the pump to form a gas segment therein following the rinse solution slug. As air flows in tube 22, the respective reagents are aspirated in the tubes 36 and 38. However, the time duration of the probe travel to the last-mentioned cup 12 is relatively short and the amounts of reagents aspirated in this interval are relatively very small. The probe is then immersed in the first sample while the valve assembly 26 is in the first condition so that sample is aspirated and flows through the tube 22, and aspiration and flow of the reagents in the respective tubes 36 and 38 is continued. The aspiration rates of each of the tubes 22, 36 and 38 may be 0.2 ml/min. for example. This flow of sample and reagents, which is combined in tube 38 on the pressure side of the pump, forms a sample-reagent slug in the tube 38 which is segmented by addition of gas thereto through pump tube 32.

When the probe 16 leaves the first sample on return movement to the wash receptacle 20 with the valve assembly 26 in the first condition, air is aspirated into the probe and flows through the tube 22 to tube 38 to form an air segment following the sample-reagent slug. During the brief time of the probe movement to the wash receptacle 20, the reagents continue to be aspirated in the respective tubes 36 and 38, the amounts of reagents aspirated in this interval being relatively very small. Prior to immersion of the probe 16 in the liquid of the wash receptacle, the valve assembly 26 is switched by the timer 28 to the second condition in which rinse solution flows once again through the pump tube 32 into the pump tube 38 to follow the last-mentioned air segment. The second sample in a cup 12 is moved to the offtake station. The cycle is repeated for the second and subsequent samples, and in this manner a segmented sample stream is caused to flow in the tube 38.

The labeled reagent which flows into the tube 38 on the suction side of the pump 24 is prepared in the apparatus and in the manner hereinafter discussed. A compressible pump tube 46 extends through the pump 24 and has an inlet end coupled to a non-illustrated source of purified HGH in solution. The purified HGH in solution is a reagent starting material designated Ag'. If the antigen of the sample is not a peptide, unlike the present example, the antigen of the reagent starting material Ag' must include a peptide tag previously applied to it as is known in radioimmunoassay. The addition of a peptide tag to a non-peptide antigen can be carried out in a variety of conventional ways, depending upon the chemical functionality of the last-mentioned antigen. Normally a carboxyl or amino group is linked to one of the functional groups of the antigen, either directly or through some intermediate chemical linkage. It is important in this addition to minimize the change in chemical structure of the antigen around its immunoreactive center.

A compressible pump tube 48, having an inlet and coupled to a non-illustrated source of a solution of a radioisotope such as $^{125}I$ or $^{131}I$, extends through the pump 24 and has an outlet end coupled to an intermediate portion of the tube 46 on the pressure side of the pump 24. Similarly, a compressible pump tube 50, having an inlet end coupled to a non-illustrated source of chloramine T in solution, extends through the pump 24 and has an outlet end coupled to an intermediate portion of the tube 46 downstream from junction of the latter with the tube 48. The outlet end of tube 46 is coupled to the inlet end of mixing coil 52. The outlet of coil 52 is coupled to the inlet end of the tube 34. The outlet end of tube 54 is coupled to the input of mixing coil 56 which has an outlet coupled to the inlet end of tube 58. Coupled intermediate the ends of the tube 54 is the outlet end of compressible pump tube 60 which tube 60 extends through the pump 24 and has an inlet end coupled to a non-illustrated source of sodium metabisulfite in solution. In operation of the thus-far-discussed apparatus for preparing reagent, there is added sequentially to the liquid stream of starting material Ag' flowing in pump tube 46 the radioactive iodine $^{125}I$ through pump tube 48 and chloromine T through the pump tube 50 which mix in coil 52 and react within approximately 2 minutes to render the starting material Ag' radioactive. Excess chloromine T is neutralized by addition through the pump tube 60 of sodium metabisulfite to the stream exiting from the coil 52 into the tube 54. This neutralization process is carried out in mixing coil 56. The stream leaving coil 56 in tube 58 contains the labeled antigen Ag* in solution and excess $^{125}I$ which unbound radioactive iodine would interfere with analysis if left in the reagent stream.

In the form of the invention of FIG. 1, the outlet end of tube 58 is coupled to an inlet of an ion-exchange column 62 having an outlet coupled to an inlet end of a tube 64. The outlet end of tube 64 is coupled to previously discussed pump tube 38 intermediate the end 40 of the tube 38 and the valve assembly 26. The excess $^{125}I$ is removed from the reagent stream flowing from the tube 58 by the ion-exchange column 62 so that the reagent stream of labeled antigen Ag* in solution flowing into tube 38 through tube 64 is free of such excess $^{125}I$. The column 62 of the single-column type may be an anion exchange column of resin of the strong base type, for example polystyrene substituted with a quarternary tri-alkyl amino group. Preferably, it is highly cross-linked, such as with 8–12% divinyl benzene for example, for minimum absorption of the labeled antigen Ag* in solution. Typically, such resins have a high selectivity for the iodine ion over the chloride ion so that such resin may be initially in the chloride ion form. The selectivity may be approximately 10 to 1 so that up to approximately ten column volumes of the reagent stream may pass through the column 62 before replacement or regeneration of the column is necessary. When flow of the labeled antigen Ag* in solution through the pump tube 38 toward the pump 24 is blocked by the valve assembly 26 as aforesaid or if the volume of such solution exceeds the demand of the pump tube 38, the antigen Ag* in solution is stored for later use in aforementioned storage coil 42 having an inlet and outlet end coupled to the end 40 of the tube 38, the other end of the coil 42 being open. The manner in which a treated and segmented sample stream is caused to flow in the tube 38 has been discussed hereinbefore.

As previously indicated, the outlet end of pump tube 38 is connected to the inlet end of incubation coil 44. This coil is temperature-controlled, and at a sampling rate of 30 samples per hour may contain at one time approximately 60 to 100 segmented samples, the samples being separated from one another by the aforementioned gas and rinse solution segments of the sample stream. The outlet of coil 44 is coupled to the inlet of reaction coil 66. The coupling of the inlet and outlet ends of the incubation coil 44 may be releasable so that the coil 44 may be temporarily removed from the system and replaced by another such coil. This permits a relatively long period of incubation of the samples within the removed coil if such a long period for sample reaction is necessary, without relatively long downtime of the system. After such incubation in the removed coil the latter is replaced in the system. Incubation times in the manual version of radioimmunoassay often exceed a day. However, relatively small antigen molecules such as digoxin require incubation of only 30 minutes in the aforementioned manual version, and in an automated system such as being discussed require only approximately 15 minutes while other heavier antigen molecules in such system requires incubation up to approximately 4 hours, owing to the precision obtainable with such instruments and the fact that in such instruments a reaction need not proceed to the point of equilibrium for obtainment of reliable analytical results. The reaction, conventional in radioimmunoassay, which occurs in the incubation coil 44 will be described hereinafter.

Such radioimmunoassay is based on the ability of the sample antigen Ag to inhibit the binding of labeled antigen Ag* by antibody $Ab_1$. The process may be considered as a competition in which Ag reduces the amount of free $Ab_1$, decreasing the availability of $Ab_1$ to Ag*. Ag* and a deficiency of $Ab_1$ are incubated together in coil 44 in the presence of the sample antigen Ag to form the complexes $AgAb_1$ and $Ag*Ab_1$, leaving some unreacted Ag* and a trace amount of unreacted Ag which trace is substantially constant from sample to sample and therefore is insignificant. Subsequent to incubation in the coil 44, the complexes $AgAb_1$ and $Ag*Ab_1$ are separated in the coil 66 from the unreacted Ag*.

The segmented samples in the coil 44, which include the last-mentioned complexes and unreacted Ag*, flow from the coil 44 one after another by the pressure differential created by the pump 24 into the reaction coil 66. The reaction coil contains in immobilized form a second antibody $Ab_2$ which may be produced in a goat and is anti-rabbit for immunochemical reaction with and binding of $Ab_1$. Antibody $Ab_2$ may be coated and immobilized on the surfaces of glass beads confined within such a coil of substantially larger internal diameter than the internal diameter of the coil 44.

However, if such coil containing such coated glass beads is utilized the gas segments of the sample stream would require removal, as in a debubbler, prior to entry of the stream into such coil, and the stream on leaving the coil would require resegmention by the introduction into the stream of immiscible fluid segments such as gas to preserve the integrity of the samples. In the presently preferred form shown by way of example in FIG. 1, the use of such large-diameter coil tubing and removal of gas segments are avoided. $Ab_2$ is coated in immobilized form on the internal surface of the coil 66 utilizing a conventional coating technique such as described in Solid-Phase Radioimmunoassay in Antibody-Coated Tubes by Kevin Catt and Geoffrey W. Tregear, Science 158: pp. 1570–1572 (1967). In the coil 66, $Ag*Ab_1$ and $AgAb_1$ become immobilized and bound to $Ab_2$ in the form of $Ag=Ab_1Ab_2$ and $AgAb_1Ab_2$, leaving the unreacted Ag* in the serum samples. It is estimated that the system life of the coil 66 may be approximately 150 to 5000 samples, that is, prior to replacement of the coil 66 which has exhausted its capacity to bind $Ab_1$.

The segmented serum samples each including the unreacted Ag* flow one after another from an outlet end of the coil 66 into a tube 68 having an inlet end coupled to the outlet end of the coil 66. The tube 68 has an outlet end for the segmented stream coupled to an inlet of a three-way solenoid-operated valve 70 which has a first outlet coupled to an inlet end of a tube 72 and a second outlet coupled to an inlet end of a tube 74. The tubes 72 and 74 have outlet ends coupled to the inlets of scintillation counters 76 and 78, respectively, which counters are operated in a conventional non-illustrated manner. Each of the scintillation counters 76, 78 has a conventional non-illustrated fluid-conveying coil therethrough having an inlet end coupled to the aforementioned inlet of the counter and an outlet end discharging from the counter to waste, the volume of such coil being equal or almost equal to the volume of a single segmented sample.

The valve 70 is controlled by the timer 28. A lead 80 has an input end connected to an output of timer 28 and an output end connected to an input of valve 70. The valve 70 is operated by the timer 28 in phased relation to the arrival at the valve 70 through the tube 68 of successive samples.

The three-way valve 70 is operative to deliver the first segmented sample to counter 76 through tube 72. The flow to counter 76 is then stopped while the second segmented sample is delivered to counter 78 through tube 74. While the flow is stopped in counter 76 and the second sample flows to counter 78, Ag* in the first sample is detected in counter 76. The first sample does not run out of counter 76 when the flow thereto is stopped by the valve 70, owing to the gas segments in the sample. When the second sample has flowed into the counter 78, valve 70 is operative to stop the flow to counter 78 after which, while the third sample is delivered to counter 76, Ag* in the second sample is detected in counter 78. The third segmented sample displaces the first sample from counter 76 to waste and washes out, with the wash liquid segment preceeding the third sample, the vestiges of the first sample in the counter 76 to prevent the contamination of the third sample by the first sample. This cycling continues until all the samples have been analyzed for Ag*.

The outputs of the scintillation counters 76 and 78 may be displayed in a conventional non-illustrated form. The concentration of antigen Ag in the samples analyzed in the described system is determined by comparing the diminished Ag* binding of the samples to that of a standard value obtained by analysis for Ag* in the system, in a manner similar to that of a sample, of a preparation of known Ag concentration.

In the modified form of the invention shown in FIG. 2, a dialyzer, indicated generally at 84, for the removal of excess $^{125}I$ in the preparation of the labeled reagent Ag* is substituted for the ion-exchange column 62 of FIG. 1. The dialyzer comprises upper and lower horizontal plates 88, 90 in opposing relationship and clamping therebetween a permeable membrane 92. The upper plate 88 has an inverted channel therein forming with the upper side of the membrane a donor stream passageway 94 having an inlet end coupled to the outlet end of tube 58 to receive the liquid stream therefrom described with reference to FIG. 1. The outlet end of the passageway 94 is coupled to the inlet end of tube 64 described with reference to FIG. 1. The lower plate 90 has a channel therein opposing the channel in the upper plate 88 and forming with the underside of the membrane a recipient stream passageway 96 for flow of such stream in a direction opposite to the direction of flow of the donor stream. The recipient stream may be water supplied from a non-illustrated pressurized source to a tube 98 having an outlet end coupled to the inlet end of passageway 96. A tube 100 has an inlet end coupled to an outlet end of passageway 96 to conduct the stream from the passageway 96 to waste. The free or excess $^{125}I$ flowing in the donor stream is removed by diffusion through the membrane 92 into the recipient stream.

While the presently preferred forms of the invention have been illustrated and described herein, it will be apparent, especially to those versed in the art, that the method and apparatus for preparation of reagents on-line in automated sample analysis may take other forms and are susceptible of various changes in details without departing from the principles of the invention.

What is claimed is:

1. A method of preparing a reagent in sample analysis, comprising the steps of:

flowing a liquid sample stream along a first conduit position;

concurrently flowing streams of different liquid reactive substances in unused condition for reagent production in respective ones of a plurality of conduits;

combining successively the outflow of said plurality of conduits for formation of and reaction in a resultant stream for flow along a second conduit portion;

removing from said resultant stream in said second conduit portion an interferent with said sample analysis to produce a reagent stream free of said interferent; and combining in a third conduit portion said sample and reagent streams from said first and second conduit portions respectively for flow in said third conduit portion toward analysis means.

2. A method as defined in claim 1, wherein: said interferent with sample analysis which is removed is an excess of one of said substances for reagent production.

3. A method as defined in claim 1, wherein: one of said substances for reagent production flowing in one of said plurality of conduits is a substance labelling said reagent for detection in said sample analysis.

4. A method as defined in claim 1, wherein: one of said substances for reagent production flowing in one of said plurality of conduits is a substance labelling said reagent for detection in said sample analysis, said one of said substances being a radioactive substance.

5. A method as defined in claim 1, wherein: one of said substances for reagent production flowing in one of said plurality of conduits is a substance for labelling a second one of said substances for reagent production flowing in a second one of said plurality of conduits, said second one of said substances being an immunoreactive substance for detection in said sample analysis.

6. A method as defined in claim 1, wherein: said interferent removal step comprises flowing said resultant stream through an ion-exchange column in said second conduit portion.

7. A method as defined in claim 1, wherein: said interferent removal step comprises dialyzing said resultant stream in said second conduit portion.

* * * * *